(12) United States Patent
Noda et al.

(10) Patent No.: US 10,451,583 B2
(45) Date of Patent: Oct. 22, 2019

(54) GAS SENSOR

(71) Applicant: DENSO CORPORATION, Kariya, Aichi-pref. (JP)

(72) Inventors: Hirofumi Noda, Kariya (JP); Hirokazu Yamada, Kariya (JP)

(73) Assignee: DENSO CORPORATION, Kariya (JP)

( * ) Notice: Subject to any disclaimer, the term of this patent is extended or adjusted under 35 U.S.C. 154(b) by 293 days.

(21) Appl. No.: 15/507,426

(22) PCT Filed: Aug. 25, 2015

(86) PCT No.: PCT/JP2015/073779
§ 371 (c)(1),
(2) Date: Feb. 28, 2017

(87) PCT Pub. No.: WO2016/031793
PCT Pub. Date: Mar. 3, 2016

(65) Prior Publication Data
US 2017/0284957 A1  Oct. 5, 2017

(30) Foreign Application Priority Data

Aug. 29, 2014 (JP) .................................. 2014-175864

(51) Int. Cl.
*G01N 27/409* (2006.01)
*G01M 15/10* (2006.01)
*G01N 27/406* (2006.01)

(52) U.S. Cl.
CPC ........ *G01N 27/409* (2013.01); *G01M 15/104* (2013.01); *G01N 27/4062* (2013.01)

(58) Field of Classification Search
CPC ........................... G01N 27/406–27/441; G01N 33/0004–33/00075; G01N 27/409; G01N 27/4062; G01M 15/10
See application file for complete search history.

(56) References Cited

U.S. PATENT DOCUMENTS

| 6,609,922 B2 * | 8/2003 | Torii ................ H01R 13/6315 439/247 |
| 2001/0025522 A1 * | 10/2001 | Kojima .............. G01N 27/4071 73/31.05 |

(Continued)

FOREIGN PATENT DOCUMENTS

| JP | 2005-77122 | 3/2005 | |
| JP | 2005077122 A * | 3/2005 | ......... G01N 27/4062 |

(Continued)

OTHER PUBLICATIONS

Nakajima et al. (JP 2012/154773 A, machine translation) (Year: 2012).*

(Continued)

*Primary Examiner* — Maris R Kessel
*Assistant Examiner* — Joshua L Allen
(74) *Attorney, Agent, or Firm* — Nixon & Vanderhye PC

(57) ABSTRACT

The gas sensor is equipped with a sensor device, a plurality of electrode springs contacting with electrodes and of the sensor device, an insulator retaining the electrode springs, and a plurality of leads connected to the respective electrode springs. Each of the electrode springs includes a retained portion retained by the insulator and a contact portion which is bent and inclined from the retained portion toward a front end side of the sensor device in the lengthwise direction. The contact portion is elastically deformed in contact with the electrode. Each of the electrode springs also includes a bent portion between the contact portion and the retained portion. The bent portion constitutes a base end of the contact portion and is oriented toward the base end side of the gas sensor in the lengthwise direction, thereby enabling the length of the sensor device to be decreased and improving the heat resistance of the electrode springs.

7 Claims, 4 Drawing Sheets

(56) References Cited

U.S. PATENT DOCUMENTS

| | | | | |
|---|---|---|---|---|
| 2002/0017127 A1* | 2/2002 | Nakano | ............. | G01N 27/4062 |
| | | | | 73/31.05 |
| 2003/0024300 A1* | 2/2003 | Kojima | ............. | G01N 27/4077 |
| | | | | 73/31.05 |
| 2003/0074950 A1* | 4/2003 | Yamada | ............. | G01N 27/4075 |
| | | | | 73/23.2 |
| 2004/0040370 A1* | 3/2004 | Kojima | ............... | G01N 27/407 |
| | | | | 73/31.05 |
| 2006/0220159 A1* | 10/2006 | Matsuo | ............. | G01N 27/4062 |
| | | | | 257/414 |
| 2010/0269568 A1* | 10/2010 | Kanao | ............... | G01N 27/4075 |
| | | | | 73/31.05 |
| 2014/0298931 A1* | 10/2014 | Oba | .................. | G01N 27/4062 |
| | | | | 73/866.5 |

FOREIGN PATENT DOCUMENTS

| | | | | |
|---|---|---|---|---|
| JP | 2005-241468 | | | 9/2005 |
| JP | 2007-163332 | | | 6/2007 |
| JP | 2007163332 | A | * | 6/2007 |
| JP | 2012-154773 | | | 8/2012 |
| JP | 2012154773 | A | * | 8/2012 |

OTHER PUBLICATIONS

International Search Report dated Oct. 27, 2015 issued in corresponding International Application No. PCT/JP2015/073779 (2 pgs.).

* cited by examiner

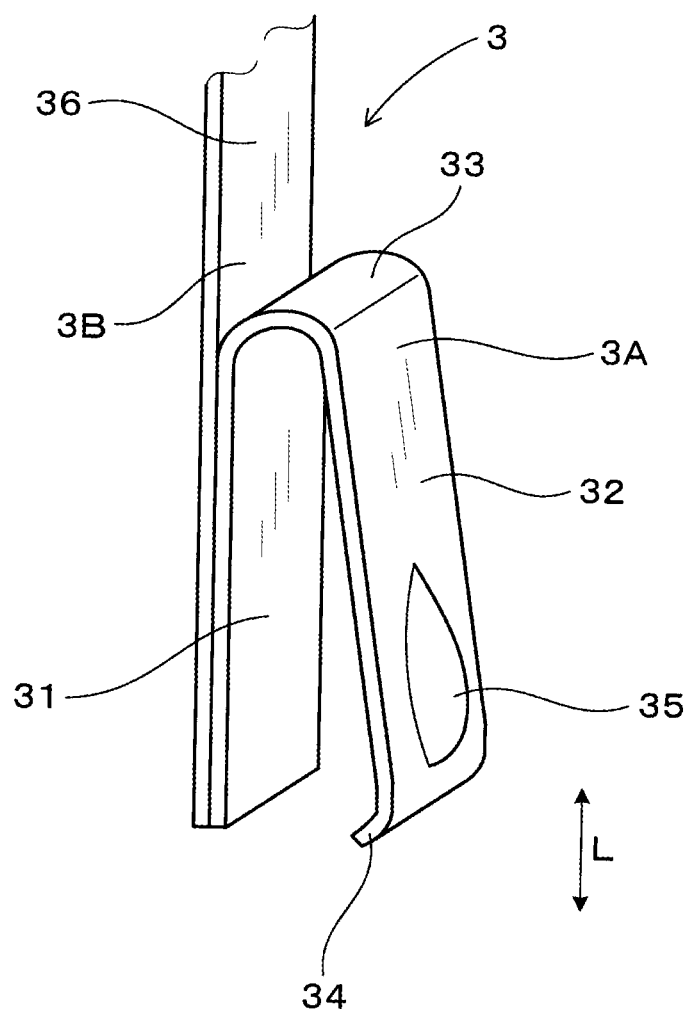

GAS SENSOR

This application is the U.S. national phase of International Application No. PCT/JP2015/073779 filed Aug. 25, 2015 which designated the U.S. and claims priority to JP Patent Application No. 2014-175864 filed Aug. 29, 2014, the entire contents of each of which are hereby incorporated by reference.

TECHNICAL FIELD

The present invention generally relates to a gas sensor designed to have an electrode spring contacting with an electrode of a sensor device.

BACKGROUND ART

Gas sensors which are designed to measure the concentration of a given gas component contained in a measurement gas have as sensor device which is made up of a solid electrolyte body and a pair of electrodes disposed on the solid electrolyte body and whose tip is disposed in a pipe through which the measurement gas flows. The sensor device has lead wires which are joined to the electrodes and extend from a base end thereof. Springs (which will also be referred to below as electrode springs) are placed in contact with the electrodes of the sensor device using an elastic force. The lead wires are connected to the electrodes through the electrode springs.

For example, Japanese Patent First Publication No. 2001-188060 discloses a gas sensor equipped with a plurality of metallic terminals which are disposed in terminal housing holes of a porcelain insulator and placed in contact with terminal electrodes disposed on a base end of a sensor device. The metallic terminals are each made up of a first portion contacting with the porcelain insulator and a second portion which is bent obliquely from the first portion and contacts with the terminal electrode. An elastic pressure is exerted on the second portion to achieve the contact with the terminal electrode.

SUMMARY OF THE INVENTION

Problem to be Solved by the Invention

However, the metallic terminals of the gas sensor, as taught in Japanese Patent First Publication No. 2001-188060, have a bent portion between the first portion contacting with the terminal electrode and the second portion contacting with the porcelain insulator. The bent portion is oriented toward the head of the sensor device. A contact portion of the metallic terminal contacting with the terminal electrode is located on a side of the base end of the sensor device. The sensor device needs to be located closer to the head of the gas sensor than to the contacting portion in a lengthwise direction of the gas sensor. It is impossible to further shorten the sensor device. In Japanese Patent First Publication No. 2001-188060, the bent portion which determines a spring property of the metallic terminal is located on a side of the head of the gas sensor that is a high-temperature side of the gas sensor. This has a disadvantage related to the heat resistance of the metallic terminals. The heat resistance of the metallic terminals is low.

The present invention was made in view of the above background. It is an object of the invention to provide a gas sensor which is capable of shortening the length of a sensor device and improving the heat resistance of the electrode springs.

Means for Solving the Problem

One aspect of the invention resides in arrangements of electrode springs of a gas sensor which includes a sensor device, a plurality of electrodes disposed on a base end side of the sensor device in a lengthwise direction of the sensor device, a plurality of electrode springs placed in contact with the respective electrodes, an insulator which retains the electrode springs, and a plurality of leads which are connected to the respective electrode springs and extend outwardly from base ends of the electrode springs in the lengthwise direction, characterized in that each of the electrode springs includes a retained portion which is retained by said insulator, a contact portion which is elastically deformed and placed in contact with said electrode, and a bent portion which is formed between said contact portion and said retained portion, and in that the contact portion extends from the retained portion through the bent portion toward a front end of the sensor device so that it slants relative to said lengthwise direction, and said bent portion is located on a base end of the contact portion.

Beneficial Effects of the Invention

The above described gas sensor features the orientation at which the electrode springs are arranged.

Specifically, each of the electrode springs has the bent portion that is the base end of the contact portion and is arranged with the bent portion facing the base end side of the gas sensor in the lengthwise direction, so that a portion of the contact portion which contacts with the electrode is located closer to the front end side than the bent portion is in the lengthwise direction, thus resulting in a decrease in distance between the front end of the sensor device and the portion of the contact portion which contacts with the electrode in the lengthwise direction, which leads to a decreased length of the sensor device.

The bent portion which determines the spring property is oriented toward the base end that is a low-temperature side of the gas sensor, thereby decreasing a risk that the bent portion is subjected to high-temperature to improve the heat resistance of the electrode springs.

It is, therefore, possible for the gas sensor to shorten the length of the sensor device, thereby improving the heat resistance of the electrode springs.

BRIEF DESCRIPTION OF THE DRAWINGS

FIG. 4 is a perspective view which illustrates an electrode spring according to an embodiment.

EMBODIMENT FOR CARRYING OUT THE INVENTION

A preferred embodiment of the above described gas sensor will be described below.

Embodiment

Figure 1:
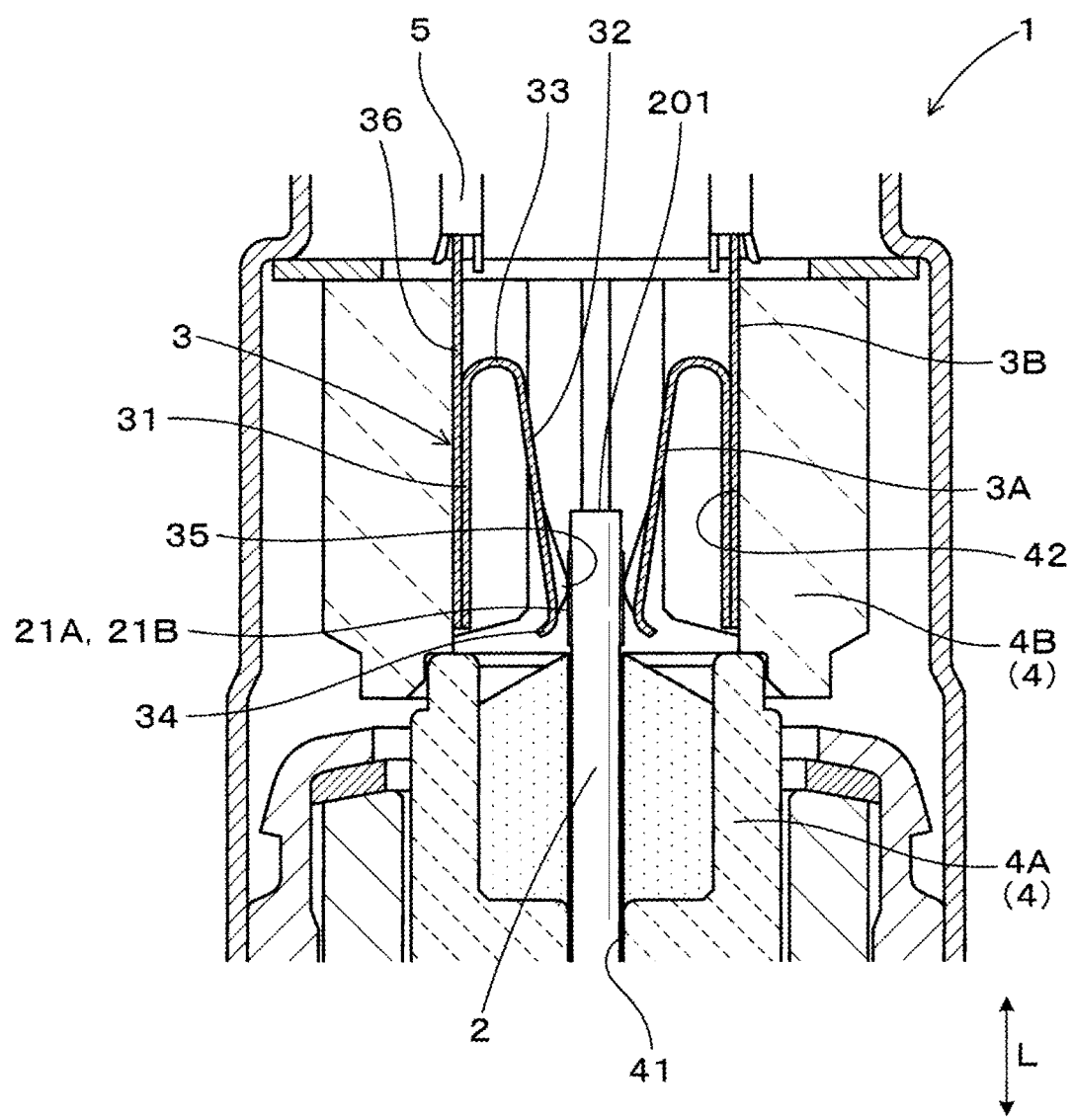
FIG. 1 is an explanatory sectional view which shows a portion of a gas sensor according to an embodiment.

The gas sensor 1 of this embodiment, as illustrated in FIG. 1, includes the sensor device 2, a plurality of electrode springs 3, the insulator 4, and a plurality of leads 5. The sensor device 2 has a given length. A lower side and an upper side of the gas sensor 1, as viewed in FIGS. 1 and 2, will be referred to below as a front end or a front end portion and a base end side or a base end portion, respectively. Similarly, a lower side and an upper side of the sensor device 2 will be referred to as a front end portion and a base end portion, respectively. The electrodes 21A and 21B are disposed on the base end portion of the sensor device in the lengthwise direction L (i.e., a lengthwise direction of the gas sensor 1). The electrode springs 3 are placed in contact with the respective electrodes 21A and 21B. The insulator 4 works as a supporting member and is made of an electrically insulating member. The insulator 4 retains the plurality of electrode springs 3. Each of the leads 5 is connected to a corresponding one of the electrode springs 3 and extends from one of the electrode springs 3 backward in the lengthwise direction L.

Each of the electrode springs 3 includes the retained portion 31 held by the insulator 4 and the contact portion 32 which is bent from the retained portion 31 and extends toward the front end side of the gas sensor 1 in the lengthwise direction L. The contact portion 32 is elastically deformed in contact with the electrode 21A or 21B. Each of the electrode springs 3 is equipped with the bent portion 33 between the contact portion 32 and the retained portion 31. The bent portion 33 is located on the base end side of the contact portion 32 and oriented to the base end side of the gas sensor 1 in the lengthwise direction L.

The gas sensor 1 of this embodiment will be described below in detail with reference to FIGS. 1 to 4.

The gas sensor 1 is installed in an exhaust pipe of an internal combustion engine and used in measuring the concentration of specified gas contained in exhaust emissions. The sensor device 2 of this embodiment is made up of a plate-like solid electrolyte body having oxygen ion conductivity, an insulator stacked on the solid electrolyte body, and a heater stacked on the solid electrolyte body. A measured gas space into which measurement gas (i.e., exhaust gas) is admitted is formed between one surface of the solid electrolyte body and the insulator. A reference gas space is formed between the other surface of the solid electrolyte body and the heater. FIG. 1 schematically illustrates the electrodes 21A and 21B.

The insulator 4 is, as illustrated in FIG. 1, made of an assembly of the first insulator 4A retaining the sensor device 2 and the second insulator 4B which retains the electrode springs 3 on the base end side of the first insulator 4A. The sensor device 2 is retained by the first insulator 4A within the insertion hole 41 formed in a central portion of the first insulator 4A. The front end portion of the sensor device 2 protrudes from the first insulator 4A and is exposed to the measurement gas. The retained portion 31 of the first member 3A, as will be described later, and the second member 3B of the electrode spring 3 are retained by an inner peripheral surface of the mount hole 42 formed in the central portion of the second insulator 4B. The first insulator 4A and the second insulator 4B are placed in contact with each other and engage each other in a concave-convex form.

Figure 2:
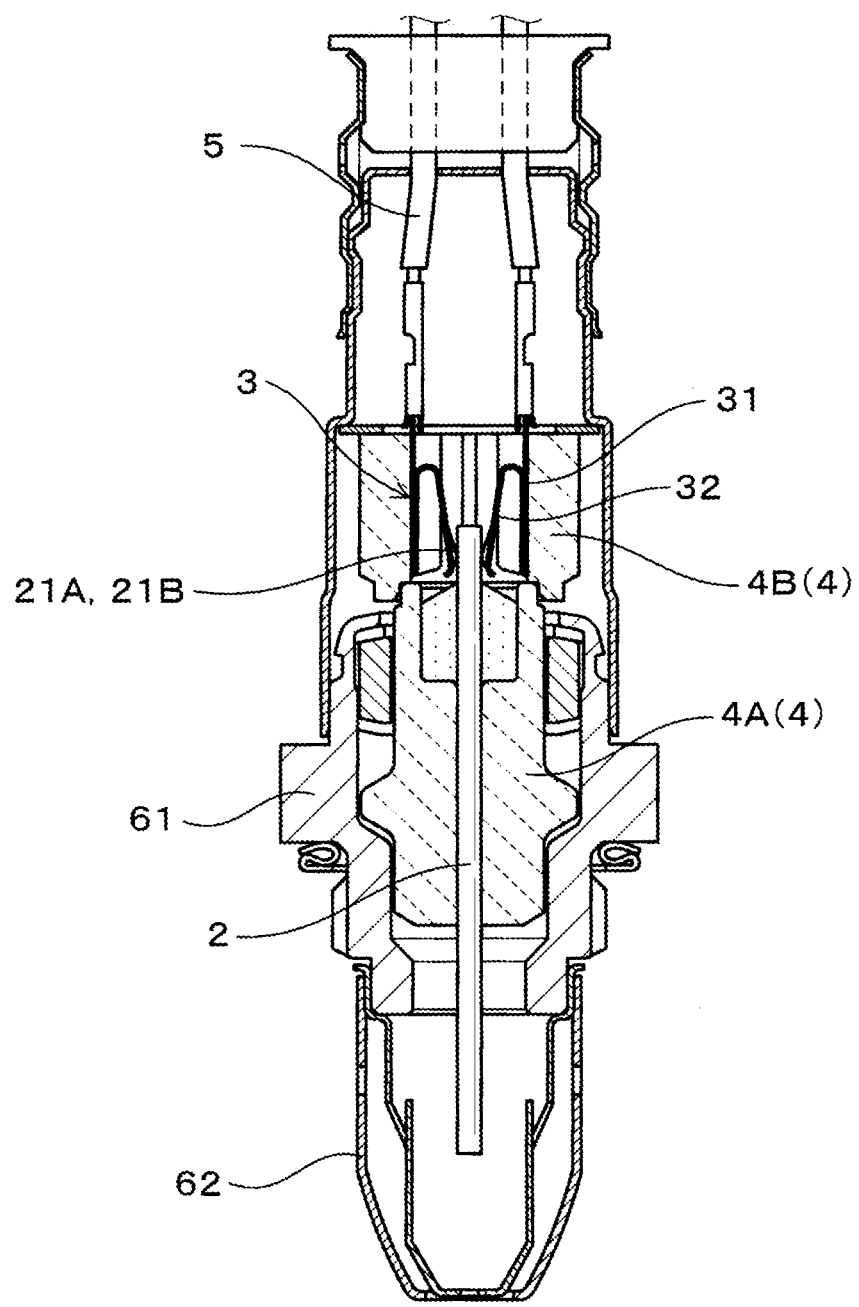
FIG. 2 is an explanatory sectional view which shows a gas sensor according to an embodiment.

The first insulator 4A is, as can be seen in FIG. 2, retained by the housing 61. The cover 62 is mounted on the housing 61. The cover 62 covers the front end portion of the sensor device 2 which protrudes from the first insulator 4A and the housing 61.

Figure 3:
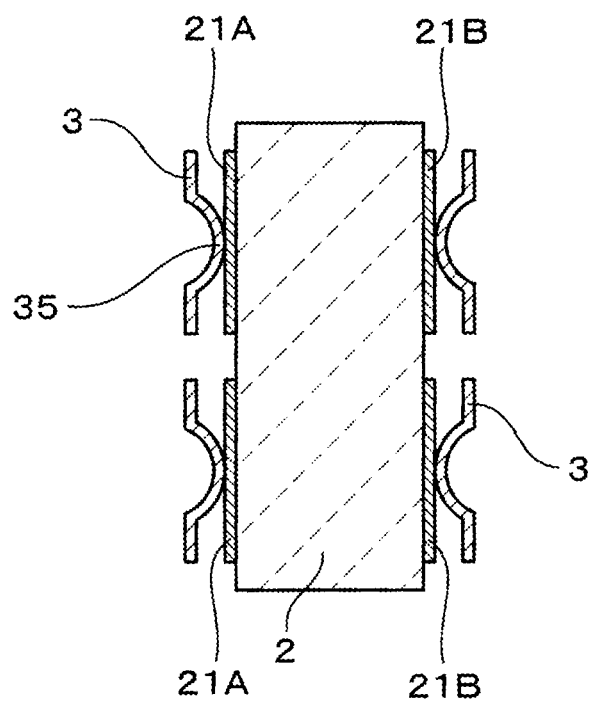
FIG. 3 is an explanatory view which illustrates contact of each electrode spring with one electrode of a sensor device using a section perpendicular to a lengthwise direction of the sensor device.

The electrodes 21A and 21B of the sensor device 2, as illustrated in FIG. 3, include a pair of sensor electrodes 21A which extend from the surface of the solid electrolyte body toward the base end side in the lengthwise direction L and a pair of heater electrodes 21B which extend from a heating element arranged inside the heater. The sensor electrodes 21A are disposed on the front end side of the solid electrolyte body in the lengthwise direction L and connect with measurement electrodes which are provided on the solid electrolyte body and placed in contact with the measurement gas and the reference gas. The heater electrodes 21B are joined to the heating element of the heater disposed on a location opposed to the measurement electrodes.

The sensor electrodes 21A are disposed on one of two major opposed surfaces of the sensor device 2 and arranged adjacent each other in a direction perpendicular to the lengthwise direction L. The heater electrodes 21B are disposed on the other surface of the sensor device 2 and arranged adjacent each other in a direction perpendicular to the lengthwise direction L.

To the pair of sensor electrodes 21A and the pair of heater electrodes 21B, the electrode springs 3 and the leads 5 are joined. The sensor electrodes 21A may be used as electrodes for measuring the concentration of oxygen, an A/F (air-fuel ratio), or the concentration of a given gas component. Two or more pairs of sensor electrodes 21A may be provided depending on intended use.

The electrode spring 3 is, as illustrated in FIG. 4, made of a plate spring and includes the first member 3A and the second member 3B. The first member 3A is formed by bending a plate at a major surface thereof into a substantially U-shape. The first member 3A constitutes the contact portion 32 and the retained portion 31. The second member 3B is laid to overlap the retained portion 31 of the first member 3A. The base end portion of the second member 3B in the lengthwise direction L protrudes from the retained portion 31 of the first member 3A to the base end side of the gas sensor 1 and has a joint portion 36 to which the lead 5 is connected. In other words, the joint portion 36 constitutes a base end of the electrode springs 3. The retained portion 31 of the first member 3A and the second member 3B are welded together. The first member 3A is made from a spring material. The second member 3B is made from steel which is weldable to the first member 3A.

If the whole of the electrode spring 3 is formed by bending a single member, it will cause a bend to be formed at a front end of a portion of the electrode spring 3 which constitutes the retained portion 31. The bend has a ball-like bulge. The bend undesirably occupies space both in the lengthwise direction L and in the width-wise direction in which the contact portion 32 and the retained portion 31 face each other, which may result in an increased side of the second insulator 4B which retains the electrode springs 3, thus leading to an increase in overall size of the gas sensor 1.

The electrode spring 3 is made up of two discrete parts: the first member 3A and the second member 3B which are welded together as a single unit, thereby alleviating the above described problem.

The electrode spring 3 may be formed by a bar spring made of a bent bar. The bar is made up of two discrete parts for improving the above problem. In the case where the electrode spring 3 is made of a bar member, a width-wise dimension of a portion of the second insulator 4B required to retain the electrode springs 3 is permitted to be decreased, which will lead to a further reduced size of the gas sensor 1.

The contact portion 32 is shaped so that it is inclined to be farther away from the retained portion 31 as approaching the front end side in the lengthwise direction L. In other words, the contact portion 32 extends from the retained portion 31 through the bent portion 33 toward the front end of the sensor device 2 in a slant form at a given angle relative to the lengthwise direction L (i.e., the length of the sensor device 2, the length of the gas sensor, or the length of the joint portion 36). The bent portion 33 between the contact portion 32 and the retained portion 31 is of a U-shape and has a corner with a curved or rounded surface or a bent surface.

The contact portion 32 has a guide portion 34 at the front end thereof. The guide portion 34 works to guide the contact portion 32 toward the electrodes 21A and 21B when the contact portion 32 is brought into contact with the electrode 21A or 21B. The guide portion 34 is of a substantially L-shape or J-shape and inclined to be closer to the retained portion 31 as approaching the front end side in the lengthwise direction L.

The front end portion of the contact portion 32, as illustrated in FIG. 4, has formed thereon the protrusion 35 which is placed in contact with the electrode 21A or 21B. The protrusion 35 is made of a portion of a plate member constituting the front end portion of the contact portion 32 which bulges from an outer surface of the contact portion 32 (i.e., an outer surface of the contact portion 32 which is shaped to be bent relative to the retained portion 31).

The electrode spring 3 is retained in the mount hole 42 of the second insulator 4B with the protrusion 35 placed in contact with the electrode 21A or 21B provided on the base end side of the sensor device 2.

The arrangement of the electrode springs 3 will now be considered in terms of orientation within the gas sensor of this embodiment.

Specifically, each of the electrode springs 3 has the bent portion 33 that is the base end of the contact portion 32 and is arranged inside the gas sensor 1 with the bent portion 33 facing the base end side of the gas sensor 1 in the lengthwise direction L, so that the protrusion 35 of the contact portion 32 is located closer to the front end side of the gas sensor 1 than the bent portion 33 is in the lengthwise direction L, thus resulting in a decrease in length of the sensor device 2, i.e., distance between the front end of the sensor device 2 and the protrusion 35 in the lengthwise direction L. This also results in a decrease in distance between the front end of the sensor device 2 and the base end 201 in the lengthwise direction L.

The bent portion 33 which determines the spring property of the electrode spring 3 is oriented toward the base end that is a low-temperature side of the gas sensor 1. A portion of the contact portion 32 and the bent portion 33 of the electrode spring 3 is located closer to the base end side of the gas sensor 1 than the base end 201 of the sensor device 2 is in the lengthwise direction L, thereby resulting in an increased distance between the front end portion of the sensor device 2 which is subjected to high-temperature and the bent portion 33, which leads to a decreased risk that the bent portion 33 is heated to high-temperatures. This results in enhanced heat-resistance of the electrode springs 3. A portion of the contact portion 32 and the bent portion 33 is located closer to the base end side than the base end 201 of the sensor device 2 is in the lengthwise direction L, thereby permitting the length of the sensor device 2 to be shortened in the lengthwise direction L.

The arrangement of the electrode springs 3 in the gas sensor 1, therefore, enables the length of the sensor device 2 in the lengthwise direction L to be decreased and improves the heat resistance of the electrode springs 3.

The invention claimed is:

1. A gas sensor comprising:
    a sensor device having a length with a front end and a base end opposed to the front end, the front end of the sensor device being configured to be exposed to gas,
    a plurality of electrodes disposed on the base end of the sensor device,
    a plurality of electrode springs placed in contact with the respective electrodes, each of the electrode springs having a front end and a base end, the front end of the electrode spring being located closer to the front end of the sensor device than the base end of the electrode spring is,
    an insulator which retains the electrode springs, and
    a plurality of leads which are connected to the respective electrode springs and extend outwardly from the base ends of the electrode springs, wherein:
    each of the electrode springs includes:
        a retained portion which is retained by said insulator, the retained portion having a front end and a base end, the front end of the retained portion being located closer to the front end of the sensor device than the base end of the retained portion is,
        a contact portion which has a front end and a base end, the front end of the contact portion being located closer to the front end of the sensor device than the base end of the contact portion is, the contact portion being inclined relative to the retained portion, bent in a turned form from the base end of the retained portion so as to face the retained portion, and placed in contact with said electrode, and
        a bent portion which is formed between and integrally connects the base end of said contact portion and the base end of said retained portion such that each of the electrode springs forms a member that continuously extends from the retained portion to the bent portion and from the bent portion to the contact portion,
    the contact portion is in contact with the electrode using spring property of the bent portion, and
    the contact portion is located closer to the front end of the sensor device than the bent portion in a lengthwise direction of the sensor device.

2. The gas sensor as set forth in claim 1, wherein the front end portion of said contact portion has a protrusion placed in contact with said electrode.

3. The gas sensor as set forth in claim 1, wherein said contact portion is shaped so that the contact portion is inclined to be farther away from said retained portion as approaching a front end side of the sensor device in the lengthwise direction, and said contact portion has a guide portion at the front end thereof, the guide portion being inclined to be closer to the retained portion as approaching the front end side of the sensor device in the lengthwise direction and configured to guide the contact portion to the electrode when the contact portion is brought into contact with the electrode.

4. The gas sensor as set forth in claim 1, wherein said bent portion is located outside the base end of the sensor device in the lengthwise direction.

5. The gas sensor as set forth in claim 1, wherein said electrode spring is formed by a plate spring made of a plate material bent to a plate surface direction or a bar member which is bent.

6. The gas sensor as set forth in claim 1, wherein said electrode spring is made up of a first member and a second member, the first member constituting said contact portion and said retained portion, the second member being laid to overlap a portion of the first member which constitutes the retained portion, and the second member has a joint portion to which the lead is connected, the joint portion extending in the lengthwise direction and constituting the base end of the electrode spring.

7. The gas sensor as set forth in claim 6, wherein a portion of the first member constituting said retained portion and the second member are welded together.

* * * * *